(12) United States Patent
Ulinskas et al.

(10) Patent No.: US 10,188,481 B2
(45) Date of Patent: Jan. 29, 2019

(54) BEAM GUIDE FOR OPHTHALMIC SURGICAL ILLUMINATION

(71) Applicant: Novartis AG, Basel (CH)

(72) Inventors: Vit Ulinskas, Tustin, CA (US); Michael J. Papac, North Tustin, CA (US)

(73) Assignee: Novartis AG, Basel (CH)

( * ) Notice: Subject to any disclaimer, the term of this patent is extended or adjusted under 35 U.S.C. 154(b) by 108 days.

(21) Appl. No.: 14/973,187

(22) Filed: Dec. 17, 2015

(65) Prior Publication Data

US 2017/0172691 A1 Jun. 22, 2017

(51) Int. Cl.
| A61B 90/30 | (2016.01) |
| A61B 3/00 | (2006.01) |
| A61B 3/10 | (2006.01) |
| G02B 6/35 | (2006.01) |
| G02B 6/42 | (2006.01) |
| G02B 27/14 | (2006.01) |
| G02B 6/00 | (2006.01) |
| A61F 9/007 | (2006.01) |

(52) U.S. Cl.
CPC .......... *A61B 90/30* (2016.02); *A61B 3/00* (2013.01); *A61B 3/0033* (2013.01); *A61B 3/0075* (2013.01); *A61B 3/10* (2013.01); *G02B 6/00* (2013.01); *G02B 6/351* (2013.01); *G02B 6/3514* (2013.01); *G02B 6/4256* (2013.01); *G02B 27/14* (2013.01); *A61B 2090/306* (2016.02); *A61F 9/007* (2013.01)

(58) Field of Classification Search
CPC ........... A61B 9/30; A61B 3/10; A61B 3/0075; A61B 3/0033; A61B 2090/306; A61F 9/007; G02B 27/14; G02B 6/4256; G02B 6/3514

USPC ........................................................ 351/221
See application file for complete search history.

(56) References Cited

U.S. PATENT DOCUMENTS

| 6,152,577 A | 11/2000 | Rizkin et al. |
| 7,933,056 B2* | 4/2011 | Tsao ....................... G02B 7/102 |
| | | 359/209.1 |
| 2014/0347629 A1 | 11/2014 | Donitzky et al. |

FOREIGN PATENT DOCUMENTS

| EP | 1769733 A2 | 4/2007 |
| JP | H11314184 A | 11/1999 |

\* cited by examiner

*Primary Examiner* — Jack Dinh (57) ABSTRACT

An ophthalmic illumination apparatus can include a movable support. The apparatus can also include an optical array coupled to the movable support and positioned to interact with a light beam from a light source. The optical array can include first and second optical elements. The first optical element can be configured to reflect and transmit first associated amounts of the light beam. The second optical element can be configured to reflect and transmit second associated amounts of the light beam different than the first optical element. The apparatus can further include a drive mechanism coupled to the movable support. The drive mechanism can be configured to cause the movable support to selectively move the optical array such that the light beam is selectively incident upon one of the first optical element or the second optical element. Associated devices, systems, and methods are also provided.

14 Claims, 7 Drawing Sheets

BEAM GUIDE FOR OPHTHALMIC SURGICAL ILLUMINATION

BACKGROUND

Technical Field

Embodiments disclosed herein can be related to ophthalmic illumination systems. More specifically, embodiments described herein can relate to splitting a single light beam from a light source into multiple beams. One or more of the multiple beams can be transmitted to a surgical field, such as a patient's eye.

Related Art

Ophthalmic microsurgical procedures can require precision cutting and/or removing of various body tissues of the patient's eye. The patient's eye can be illuminated during the surgical procedure with an endo-illuminator or other illumination probe. A surgeon can hold the endo-illuminator in one hand while holding a surgical probe in the other hand. The endo-illuminator can transmit illuminate the patient's eye with light output by a light source. The light source can be characterized by an output power. The output power of the light source can sometimes exceed the amount of light transmittable by the endo-illuminator. In such instances, the light from the light source cannot be directly coupled into the endo-illuminator. Efficacy of the surgical procedure can depend on the appropriate amount of light being transmitted to the patient's eye.

Accordingly, there remains a need for improved devices, systems, and methods that facilitate reliable transmission of light from the light source to the patient's eye by addressing one or more of the needs discussed above.

SUMMARY

The presented solution fills an unmet medical need with a unique solution to split a single light beam output by a light source into multiple beams before being transmitted to a patient's eye. An optical array can be positioned in the optical path of the light beam output by the light source. The optical array can include one or more optical elements that reflect a portion of the light beam and transmit a portion of the light beam. Different optical elements can reflect and transmit different amounts of light. The optical array can be moved so that the light beam from the light source interacts with a desired optical element. The beam guide can be moved by a drive mechanism, such as a motor. The beam guide and the drive mechanism can each be attached to an intermediary movable support. The drive mechanism can move the movable support which in turn moves the beam guide.

Consistent with some embodiments, an ophthalmic illumination apparatus can be provided. The apparatus can include a movable support. The apparatus can also include an optical array coupled to the movable support and positioned to interact with a light beam from a light source. The optical array can include first and second optical elements. The first optical element can be configured to reflect and transmit first associated amounts of the light beam. The second optical element can be configured to reflect and transmit second associated amounts of the light beam different than the first optical element. The apparatus can further include a drive mechanism coupled to the movable support. The drive mechanism can be configured to cause the movable support to selectively move the optical array such that the light beam is selectively incident upon one of the first optical element or the second optical element.

Consistent with some embodiments, a method of ophthalmic surgical illumination can be provided. The method can include guiding, using an optical array, a reflected portion of a light beam from a light source and a transmitted portion of the light beam from the light source. The optical array can include first and second optical elements. The first optical element can be configured to reflect and transmit first associated amounts of the light beam. The second optical element can be configured to reflect and transmit second associated amounts of the light beam different than the first optical element. The method can also include moving the optical array by moving a movable support using a drive mechanism. The optical array can be coupled to the movable support such that the light beam is selectively incident upon one of the first optical element or the second optical element.

Additional aspects, features, and advantages of the present disclosure will become apparent from the following detailed description.

In the drawings, elements having the same designation have the same or similar functions.

DETAILED DESCRIPTION

In the following description, specific details can be set forth describing certain embodiments. It will be apparent, however, to one skilled in the art that the disclosed embodiments may be practiced without some or all of these specific details. Specific and/or illustrative, but not limiting, embodiments can be presented herein. One skilled in the art will realize that other material, although not specifically described herein, can be within the scope and spirit of this disclosure.

The present disclosure describes devices, systems, and methods of splitting a single light beam from light source using an optical array. The optical array having one or more optical elements that each reflect a portion of the light beam and transmit a portion of the light beam. Thus, the single light beam from the light source can be split into a reflected light beam and a transmitted light beam. These reflected and transmitted beams can be directed to different ports of a surgical console or illumination subsystem thereof. An optical fiber of an illumination device can be coupled to one of the ports. The illumination device can deliver the reflected or transmitted beam to a surgical field, such as a patient's eye, to illuminate the surgical field. The optical element(s) of the optical array can reflect and transmit different amounts of light. Thus, the amount of light delivered to each port can depend on the optical element that interacts with the light. The optical array can be moved such that the light beam interacts with the desired optical element. A drive mechanism, such as a motor, can move the optical array. The optical array and drive mechanism can each be connected to an intermediary movable support. The drive mechanism can move the movable support such that the optical array correspondingly moves. The drive mechanism can impart motion to the movable support via a coupling mechanism, such as a belt and pulley system, a rack and pinion system, and a lead screw and bearing block system.

The devices, systems, and methods of the present disclosure provide numerous advantages, including: (1) minimizing distortion in light beam(s) resulting from drive mechanism vibrations by coupling the drive mechanism to the intermediary movable support; (2) improving light alignment by moving the optical array with relatively high precision coupling mechanism; (3) minimizing compounding effect of tolerances of different components by coupling the drive mechanism and the optical array to the intermediary movable support; and (4) achieving narrow tolerance requirements for light beam(s) as a result of high stability.

Figure 1:
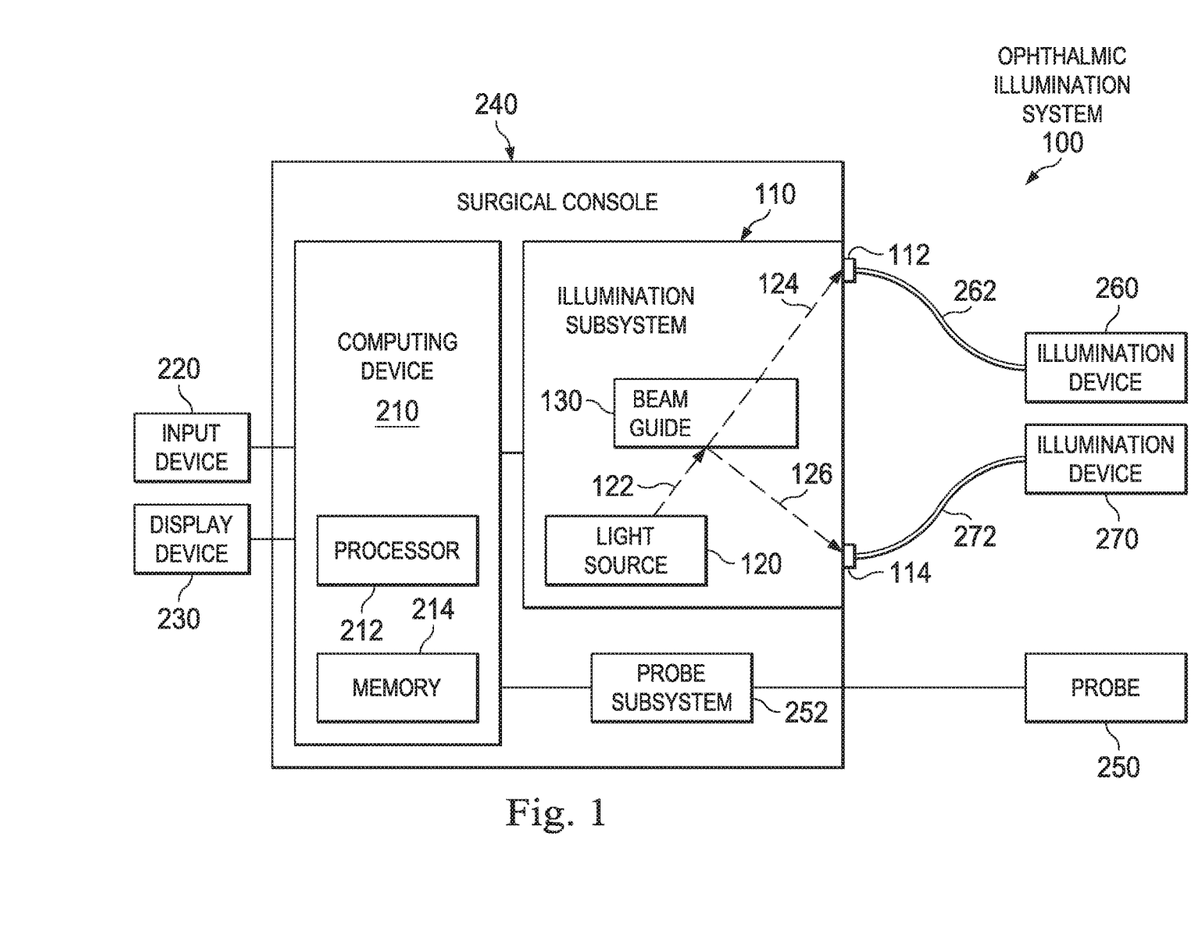
FIG. 1 is a schematic diagram of an ophthalmic illumination system.
Figure 2:
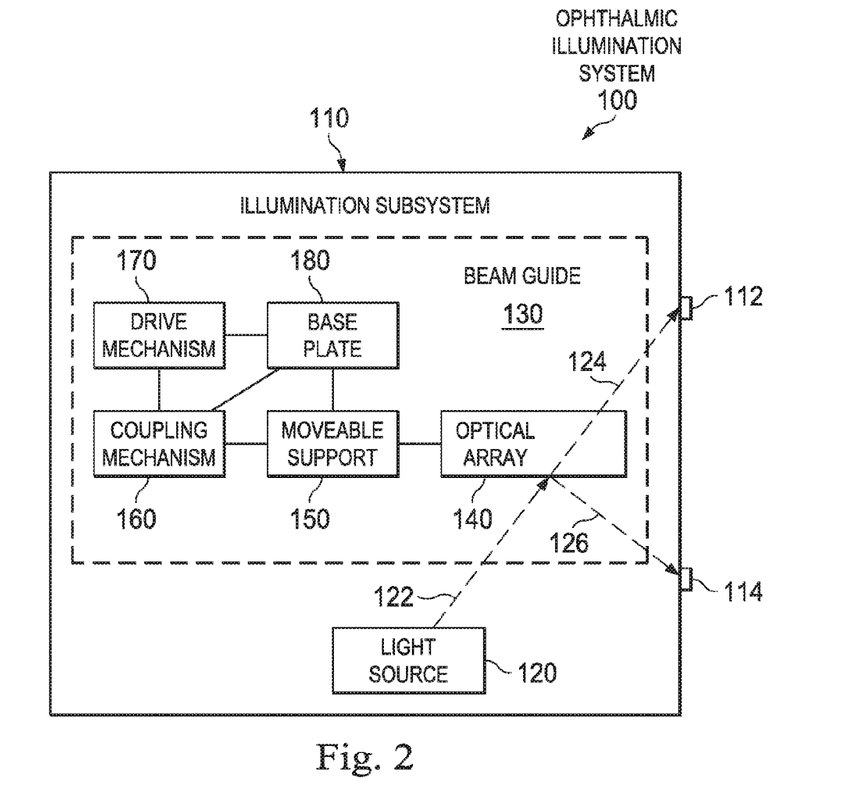
FIG. 2 is a schematic diagram of an illumination subsystem of an ophthalmic illumination system.

FIGS. 1 and 2 illustrate an example ophthalmic illumination system 100. FIG. 1 can be a schematic diagram of the ophthalmic illumination system 100. FIG. 2 can be a schematic diagram of an illumination subsystem 110 of the ophthalmic illumination system 100. The ophthalmic illumination system 100 can include a beam guide 130. The beam guide 130 can include a movable support 150 and an optical array 140 coupled to the movable support 150. The optical array 140 can be positioned to interact with a light beam 122 from a light source 120. The optical array 140 can include multiple optical elements, such as one or more of the optical elements 142, 144, 146, 148 illustrated in FIGS. 3A-9. One of the optical elements can be configured to reflect and transmit first associated amounts of the light beam 122. Another one of the optical elements can be configured to reflect and transmit second associated amounts of the light beam 122. The first and second associated amounts of the light beam 122 can be different. The beam guide 130 can also include a drive mechanism 170 coupled to the movable support 150. For example, the drive mechanism 170 can be coupled to the movable support 150 via a coupling mechanism 160. The drive mechanism 170 can be configured to cause the movable support 150 to selectively move the optical array 140. The light beam 122 can be selectively incident upon one of the optical elements.

The ophthalmic illumination system 100 can be used to perform various ophthalmic surgical procedures including an anterior segment procedure, a posterior segment procedure, a vitreoretinal procedure, a vitrectomy procedure, a cataract procedure, and/or other desired procedures. The surgical field can include any suitable physiology of the patient's eye, including an anterior segment, a posterior segment, a cornea, a lens, a vitreous chamber, transparent membranes, blood vessels, a retina, a macula, a foveola, a fovea centraalis, a para fovea, a perifovea, an optic disc, an optic cup, and/or other biological tissue.

The light source 120 can be configured to output the light beam 122 to illuminate the surgical field. The light source 120 can include a laser source, such as a supercontinuum laser source, an incandescent light bulb, a halogen light bulb, a metal halide light bulb, a xenon light bulb, a mercury vapor light bulb, a light emitting diode (LED), other suitable sources, and/or combinations thereof. For example, the light source 120 can be configured to output bright, broadband, and/or white light to the surgical field. The light source 120 can be configured to output any suitable wavelength(s) of light, such as a visible light, infrared light, ultraviolet (UV) light, etc. For example, the wavelength of the light beam 122 can be between approximately 250 nm and approximately 2500 nm, between approximately 250 nm and approximately 750 nm, between approximately 380 nm and approximately 750 nm, between approximately 750 nm and approximately 2500 nm, and/or other suitable values, both larger and smaller. The light source 120 can be wavelength-varying or swept light source. The light source 120 can be a fixed-wavelength light source. The light source 120 can be in communication with optics, such as lenses, mirrors, filters, and/or gratings, configured to vary the wavelength or color of the light beam 122. The light beam 122 can be a collimated beam. In that regard, the illumination subsystem 110 can include one or more additional optical components to collimate the light beam 122, such as a collimator having one or more lenses, mirrors, filters, and/or gratings. The light source 120 can be immobilized within a housing the illumination subsystem 110. As a result, the light beam 122 can be directed at a fixed location. As described herein, the optical array 140 can be moved into the optical path of the light beam 122 in manner that maintains proper positioning, leveling, and/or alignment of the optical elements 142, 144, 146, 148 with respect to the light beam 122.

Generally, the beam guide 130 and/or the optical array 140 can be characterized as a beam splitter. For example, the beam guide 130 and/or the optical array 140 can split the light beam 122 into the transmitted beam 124 and the reflected beam 126. As described herein, the amount or proportion of the light beam 122 transmitted and/or reflected can be determined by the optical element (e.g., the optical element 142) that interacts with the light beam 122. The transmitted beam 124 and the reflected beam 126 can be respectively associated with different optical paths. Each optical path can include additional components, such as a beam splitter or a beam guide to further split the transmitted beam 124 or the reflected beam 126 into multiple beams. Each optical path can also include filters, condensers, and/or other optical elements to facilitate delivery of light having the desired properties to the surgical field.

Referring again to FIGS. 1 and 2, the transmitted beam 124 can be directed to a port 112. The reflected beam 114 can be directed to a port 114. The ports 112, 114 can be disposed on an exterior of the housing of the illumination subsystem 110. The optical array 140, the movable support 150, the coupling mechanism 160, the drive mechanism 170, and the base plate 170, as well as the light source 120 can be positioned within the housing of the illumination subsystem 110. An optical fiber 262 of an illumination device 260 can be coupled to the illumination subsystem 110 at the port 112. The transmitted beam 124 can be delivered to the optical fiber 262 at the port 112. An optical fiber 272 of an illumination device 270 can be coupled to the illumination subsystem 110 at the port 114. The reflected beam 126 can be delivered to the optical fiber 272 at the port 114. The illumination device 260 and/or the illumination device 270 can selectively illuminate the surgical field. For example, a user can choose which of the illumination devices 260, 270 by selectively activating or deactivating delivery of light at the ports 112, 114, respectively. The user can be a surgeon, other medical professional, or a technician. One or both of the optical fibers 262, 272 can be used a given time. The optical fibers 262, 272 can be coupled to a single illumination device. Illumination devices 260 and/or 270 can be a spot illuminator, a chandelier illuminator, an endo-illuminator, and/or other suitable illumination probe.

The optical fibers 262 and/or 272 can be coupled to a surgical probe. For example, the surgical probe and the light source 120 can be part of a part of a therapeutic beam delivery system, such as a laser beam delivery system, a photocoagulation system, a photodynamic therapy system, a retinal laser treatment system.

Referring to FIG. 1, the optical array 140 can include one, two, three, four, five, or more optical elements configured to interact with the light beam 122 to split, reflect, and/or transmit light. The optical array 140 can be positioned in an optical path of the light beam 122 to intersect the light beam 122. Optical array 140 including three optical elements (e.g., optical elements 142, 144, 146) can be illustrated in FIGS. 3A-6C. Optical array 140 including two optical elements (e.g., optical elements 142, 144) can be illustrated in FIG. 7. Optical array 140 including four optical elements (e.g., optical elements 142, 144, 146, 148) can be illustrated in FIG. 8. Optical array 140 including one optical element (e.g., optical element 142) can be illustrated in FIG. 9. One or more of the optical elements 142, 144, 146, 148 can be made of or include glass, quartz glass, meteoritic glass, germanium, fluorite, plastic, high index plastic, Trivex, acrylic, polycarbonate, or other suitable material. The optical elements 142, 144, 146, 148 can be positioned adjacent to one another in a horizontal, vertical, and/or other suitable configuration. The optical elements 142, 144, 146, 148 can be coupled to one another, for example, using an adhesive or a mechanical attachment.

The optical elements 142, 144, 146, 148 can be configured to reflect and transmit associated amounts or proportions of the light beam 122. In that regard, each of the optical elements 142, 144, 146, 148 can be configured to reflect and transmit different percentages of the light beam 122, including between approximately 1% and approximately 99%, between approximately 10% and approximately 90%, between approximately 20% and approximately 80%, and/or other suitable values, both larger and smaller. The amount of light that is reflected and transmitted can be associated in that their sum equals 100%, including any losses as a result of imperfect reflection/transmission. For example, the optical element 142 can be configured to reflect 75% and to transmit 25% of incident light. As a result, the reflected beam 126 can have 75% of the power of the light beam 122 and the transmitted beam can have 25% of the power of the light beam 122. For example, the optical element 144 can be configured to reflect 50% and to transmit 50% of the light beam 122. For example, the optical element 146 can be configured to reflect 25% and to transmit 75% of the light beam 122. As described herein, the user can selectively move the optical array 140 and/or the optical elements 142, 144, 146, 148 into the optical path of the light beam 122 such that the light beam 122 is split in the desired manner. For example, desired amounts of light can be directed to the ports 112, 114 with the transmitted beam 124 and the reflected beam 126, respectively.

The optical elements 142, 144, 146, 148 can be suitably arranged to facilitate partial transmission and partial reflection of the light beam 122. For example, the optical elements 142, 144, 146, 148 can include a glass prism, a metallic-coated mirror, a dichroic filter, a dichroic mirror, a dichroic mirrored prism, a notch filter, a hot mirror, and/or a cold mirror. The optical elements 142, 144, 146, 148 can include one or more optical coatings and/or embedded particles. In that regard, the optical coating(s) and/or embedded particle(s) can be selected and/or applied in a manner to achieve desired transmission/reflection amounts. The optical coating(s) and/or embedded compound(s) can include plastic, metal oxide, zinc sulfide, zinc selenide, sodium aluminum fluoride, natural and/or synthetic dye, organic and/or inorganic dye, colloidal dye, a rare earth transition element, or other suitable material(s). The optical elements 142, 144, 146, 148 can split the light beam 122 based on interference, such as with a multilayer dielectric coating. Transmission and reflection of the light beam 122 can be wavelength-dependent. For example, the optical elements 142, 144, 146, 148 can be a long pass, short pass, bandpass, band stop, and/or other suitable filter. The optical elements 142, 144, 146, 148 can split the light beam 122 using a deposited metal. The pattern and/or density of the deposited metal on the optical elements 142, 144, 146, 148 can determine the amounts of reflection and transmission. Any suitable process can be used to dispose a material on the optical elements 142, 144, 146, 148, including physical vapor deposition, chemical vapor deposition, chemical adsorption, physical adsorption, dip coating, solvent evaporation, and/or other suitable processes.

Figure 3A:
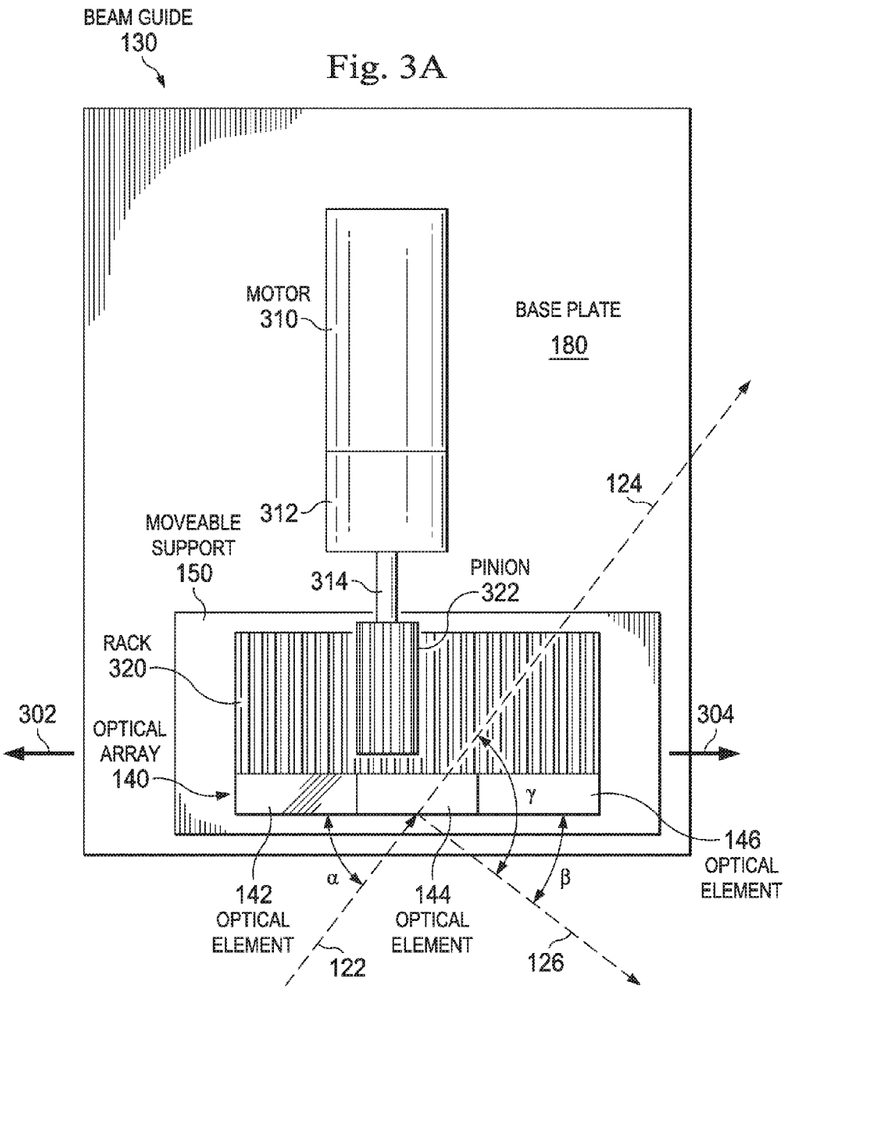
FIGS. 3A and 3B are top view illustrations of a beam guide of an ophthalmic illumination system.
Figure 3B:
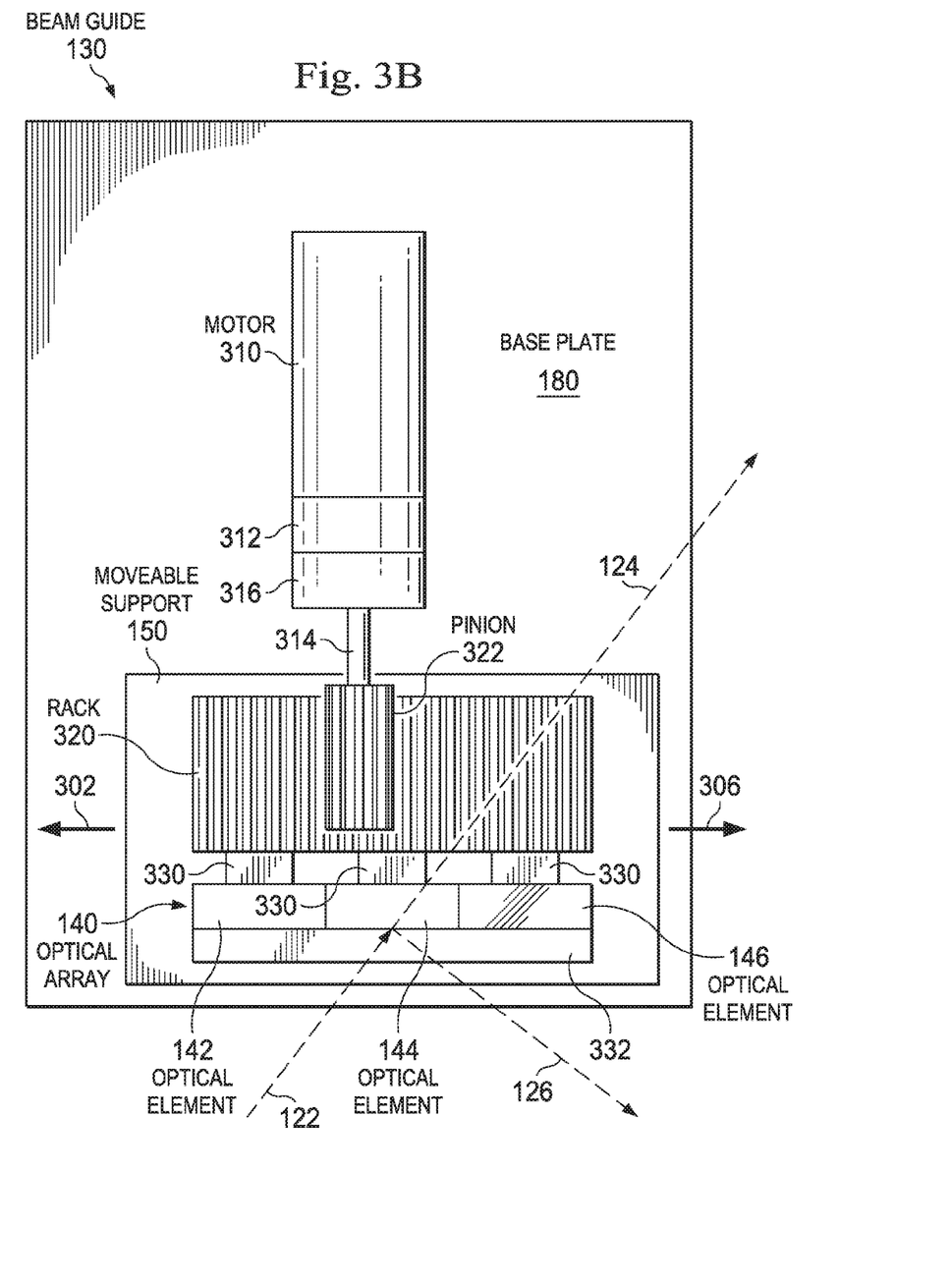
Figure 4:
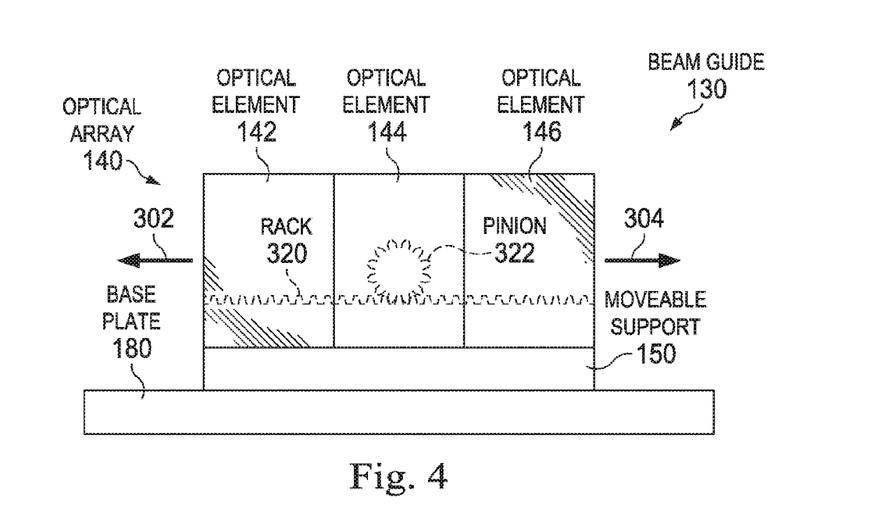
FIG. 4 is a front view illustration of a beam guide of an ophthalmic illumination system.
Figure 5:
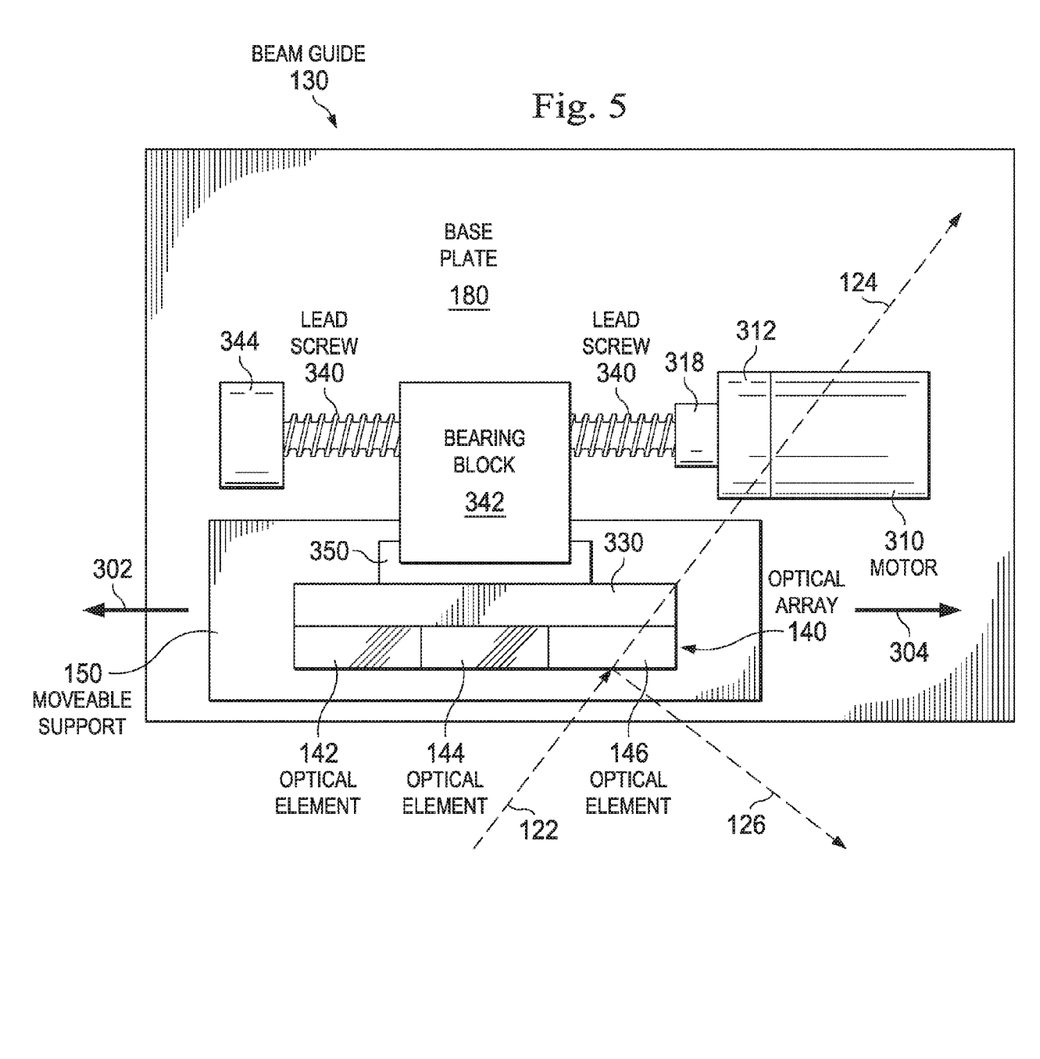
FIG. 5 is a top view illustration of a beam guide of an ophthalmic illumination system.

Referring to FIGS. 2, 3A, 3B, 4, and 5, the movable support 150 can be sized and shaped to have one or more components of the ophthalmic illumination system 100 coupled thereto. FIGS. 3A and 3B can be top view illustrations of the beam guide 130 including the movable support 150. FIG. 4 can be a front view illustration of the beam guide 130 including the movable support 150. FIG. 5 can be another top view illustration of the beam guide 130 including the movable support 150. The movable support 150 can be fabricated from any suitable material(s), such as a metal including steel. The movable support 150 can be configured to provide a solid and stable intermediary foundation for the optical array 140, the drive mechanism 170, and/or the coupling mechanism 160. For example, the optical array 150 can be mechanically attached to the movable support 150 using an adhesive, a mechanical coupling, and/or combinations thereof. For example, the optical array 150 can be fixedly and/or rigidly coupled to the movable support 150. All or a part of the coupling mechanism 160 and/or all or a part of the drive mechanism 170 can be mechanically coupled to the movable support 150. In that regard, the coupling mechanism 160 and/or the drive mechanism 170 can be directly or indirectly coupled to the movable support 150. The movable support 150 can be configured to be translated in a smooth, predictable, and/or regular manner. In that regard, the movable support 150 can be movably coupled to a base plate 180. For example, radial or conical bearings disposed between the movable support 150 and the base plate 180 can facilitate translational motion of the movable support 150 relative to the base plate 180. The movable support 150 can be configured to move side-to-side and/or up-and-down relative to the base plate 180. The movable support 150 can move in one or more directions, such as along a line or within a plane.

The base plate 180 can be sized and shaped to have one or more components of the ophthalmic illumination system 100 coupled thereto. For example, the base plate 180 can be solid and stable foundation for the movable support 150, the coupling mechanism 160, and/or the drive mechanism 170. All or part of the coupling mechanism 160 and/or the drive mechanism 170 can be mechanically attached to the base plate 180. For example, all or part of the coupling mechanism 160 and/or the drive mechanism 170 can be fixedly and/or rigidly coupled to the base plate 180. The base plate 180 can be fixed and/or immobilized with respect to the housing of the illumination subsystem 110 and/or a housing of a surgical console 240. The base plate can have a precision-ground top surface facilitating proper positioning, leveling, and/or alignment the movable support 150, the coupling mechanism 160, and/or the drive mechanism 170. For example, the movable support 150 can be translated along the level top surface of the base plate 180 such that the light beam remains aligned with the optical array 140.

The drive mechanism 170 can be any suitable device configured to impart motion to the movable support 150. For example, the drive mechanism 170 can be a motor 310, such as an electric motor. The drive mechanism 170 can be directly or indirectly coupled to the movable support 150 to cause the movable support 150 to selectively translate the optical array 140. Direct attachment of the drive mechanism 170 to the optical array 140 can be avoided. The drive mechanism 170 can be advantageously coupled to the movable support 150 via the coupling mechanism 160. For example, the drive mechanism 170 can be directly attached to a component of the coupling mechanism 160. Any unwanted mechanical attributes of the drive mechanism, such as vibration and/or misalignment, can be experienced by the coupling mechanism 160 and/or the movable support 150, rather than the optical array 140. The drive mechanism 170 can include a gearbox 312 to perform gear reduction such that the speed, acceleration, and/or other attributes associated with motion of the drive mechanism 170 and/or the movable support 150 can be controlled.

The coupling mechanism 160 can include any suitable combination of mechanical elements that couples the drive mechanism 170 and the movable support 150. The coupling mechanism 160 can also facilitate movement of the movable support 150 and corresponding movement of the optical array 140 as a result of movement of the drive mechanism 170. The optical array 140 can be moved in response a user input so that the light beam 122 interacts with a desired optical element to generate the transmitted beam 124 and the reflected beam 126. The transmitted beam 124 and the reflected beam 126 can have the desired properties, such as the amount or proportion of light from the light beam 122, based on the illumination needs of the user.

Moving the movable support 150 can include actuating the coupling mechanism 160. In that regard, one or more components of the coupling mechanism 160 can be directly attached to the drive mechanism 170. One or more components of the coupling mechanism 160 can be directly attached to the drive mechanism 170. In some examples, the coupling mechanism 160 can include belt and pulley system. The belt and pulley system can include at least two spindles, including a driver spindle, a driver pulley, a driven pulley, and one or more belts. The driver spindle and/or the driver pulley can be mechanically coupled to the drive mechanism, as such the motor 310 and/or the gearbox 312. The one or more belts can extend between the driver pulley and the driven pulley. Rotation of the driver pulley can cause rotation of the driven pulley. The driven pulley can be mechanically coupled to one or more gears. The one or more gears can be coupled to the movable support 150 and configured to translate the movable support 150. Translation of the movable support 150 can cause corresponding translation of the optical array 150.

The coupling mechanism 130 illustrated in FIGS. 3A, 3B, and 4 can be a rack and pinion system. FIGS. 3A and 3B can be top view illustrations of the beam guide 130. FIG. 4 can be a front view illustration of the beam guide 130. The movable support 150 can be movably coupled to the base plate 180. The optical array 140, including optical elements 142, 144, 146 can be directly attached to the movable support 150. The motor 310 and the gearbox 312 can be directly attached to the base plate 180. A pinion 322 can be mechanically coupled to a shaft 314 of the motor 310, such as via a shaft coupler. The optical array 140 is not directly attached to the shaft 314. Upon activation of the motor 310, the shaft 314 can rotate, causing rotation of the pinion 322. The pinion 322 can be mechanically engaged to a rack 320. For example, teeth of the pinion 322 can mechanically engage teeth of the rack 320. The rack 320 can be mechanically coupled and/or directly attached to the movable support 150. Rotation of the pinion 322 can translate the rack 320. For example, clockwise or counterclockwise rotation of the pinion 322 can translate the rack 320 in a direction 302 or a direction 304, respectively. Because of the mechanical coupling between the rack 320 and the movable support 150, the movable support 150 can correspondingly move when the rack 320 moves. For example, the movable support 150 can be translated in the directions 302, 304. Similarly, because the mechanically coupling between optical array 140 and the movable support 150, the optical array 140 can be correspondingly translated in the directions 302, 304.

As illustrated in FIGS. 3A and 3B, the light beam 122 from the light source 120 can interact with the optical element 144 to generate the transmitted beam 124 and the reflected beam 126. The optical array 140 can be translated in the direction 302, while the light beam 122 remains stationary, so that the light beam 122 interacts with the optical element 146. The optical array 140 can be translated in the direction 304, while the light beam 122 remains stationary, so that the light beam 122 interacts with the optical element 142. The properties of the transmitted beam 124 and the reflected beam 126, including the respective amount of light, can be different when the light beam 122 interacts with the optical element 142 or 146, compared to the optical element 144.

As illustrated in FIG. 3A, the light beam 122 can be characterized by angle of incidence $\alpha$ with respect to the optical element 142. The reflected beam 126 can be characterized by angle of reflection $\beta$ with respect to the optical element 142. According to the law of reflection, angle of incidence $\alpha$ can be equal to the angle of reflection $\beta$. The transmitted beam 124 and the reflected beam can be separated by angle $\gamma$. The angle $\gamma$ can be pre-determined and can include values such as 90°.

The coupling mechanism 130 illustrated in FIG. 5 can be a lead screw and bearing block system. FIG. 5 can be a top view illustration of the beam guide 130. The movable support 150 can be movably coupled to the base plate 180. The optical array 140, including optical elements 142, 144, 146 can be directly attached to the movable support 150. The motor 310 and the gearbox 312 can be directly attached to the base plate 180. A lead screw 340 can be mechanically coupled to the shaft of the motor 310, such as via the shaft coupler 318. An end bearing 344 can be fixedly and directly attached to the base plate 180. The lead screw 340 can extend between the shaft of the motor 310 and the end bearing 344. A bearing block 342 can be mechanically engaged to the lead screw 340. For example, the lead screw 340 can have any male threads, and the bearing block 342 can have corresponding female threads. Any suitable threads, including Acme threads, can be utilized for the lead screw 340 and the bearing block 342. The bearing block 342 can be configured to move along the lead screw 340. For example, the bearing block 342 can be configured to translate along the lead screw 342 in the directions 302, 304 as a result of clockwise and counterclockwise rotation of the lead screw 340. Upon activation of the motor 310, the lead screw 314 can rotate, causing movement of bearing block 342. The bearing block 342 can be mechanically coupled to the movable support 150. Accordingly, clockwise or counterclockwise rotation of the bearing block 342 can translate the movable support 150 in one or the other of directions 302, 304. Similarly, because the mechanically coupling between optical array 140 and the movable support 150, the optical array 140 can be correspondingly translated in the directions 302, 304.

In FIG. 5, the light beam 122 from the light source 120 can interact with the optical element 146 to generate the transmitted beam 124 and the reflected beam 126. The optical array 140 can be translated in the direction 340, while the light beam 122 remains stationary, so that the light beam 122 interacts with the optical element 144. The optical array 140 can be further translated in the direction 304, while the light beam 122 remains stationary, so that the light beam 122 interacts with the optical element 142. The properties of the transmitted beam 124 and the reflected beam 126, including the respective amount of light, can be different when the light beam 122 interacts with the optical element 142 or 144, compared to the optical element 146.

The bearing block 342 can be coupled to the movable support 150 via a dampening mechanism 350. Generally, the dampening mechanism 350 can be an intermediary component between the movable support 150 and one or more elements of the coupling mechanism 160. For example, the dampening mechanism 350 can be an intermediary component between the movable support 150 and the bearing block 342. The dampening mechanism 350 can be configured to minimize vibrations associated with the drive mechanism 170, such as the motor 314, and/or the coupling mechanism 160, such as the lead screw 340 and/or the bearing block 342. The dampening mechanism 350 can be implemented along with any suitable coupling mechanism 130, including the belt and pulley system and the rack and pinion system.

As illustrated in FIGS. 3B and 5, the beam guide 130 can include a stabilizer 330 positioned adjacent to the optical array 140. The stabilizer 330 can be configured stabilize the optical array 140 by minimizing undesired movement of the optical elements 142, 144, 146 during movement of the movable support 150. The stabilizer 330 can be a backing plate for mounting the optical elements 142, 144, 146. The stabilizer 330 can be provided for each of the optical elements 142, 144, 146 (FIG. 3A) or the stabilizer 330 can be provided for the all of the optical elements 142, 144, 146 (FIG. 5). The stabilizer 330 can be directly coupled to the movable support 150.

As illustrated in FIG. 3A, the beam guide 130 can include a counter stabilizer 332 positioned adjacent to the optical array 140. For example, the counter stabilizer 332 can be positioned on an opposing side of the optical array 140 relative to the stabilizer 330. The counter stabilizer 332 can be configured stabilize the optical array 140 by minimizing undesired movement of the optical elements 142, 144, 146 during movement of the movable support 150. For example, the stabilizer 330 can urge the optical array 140 against the counter stabilizer 332 to limited undesired movement of the optical elements 142, 144, 146, such as during movement of the movable support 150. The counter stabilizer 332 can be directly coupled to the movable support 150. The counter stabilizer 332 can be sized and shaped to extend across a front surface of the optical elements 142, 144, 146. The light beam 122 can be incident on the front surface. The counter stabilizer 332 can be clear such that the light beam 122 does not interact with it. Rather the light beam 122 can pass through the counter stabilizer 332 and interact with the optical element 142, 144, or 146.

The beam guide 130 can include a position sensor configured to determine a position of the optical array 140 and/or the drive mechanism 170. The position sensor can track the position of the optical array 140 and/or the drive mechanism 170 to ensure proper alignment of the light beam 122 and the optical array 140. The position sensor can be an encoder 316, as illustrated in FIG. 3B. The encoder 315 can determine and track an angular position of the shaft 314 of the motor 310. The position of the movable support 150 and/or the optical array 140 can be determined based on the angular position of the shaft 314. The position sensor can be a laser interferometer, the Hall effect sensor, or other suitable mechanism to determine and track the position of the optical array 140 and/or the drive mechanism 170. A computing device 210 can utilize the sensed position of optical array 140 and/or the drive mechanism 170 to generate a control signal for the drive mechanism 170 to move movable support 150 and/or the optical array 140 based on a user input.

Figure 6A:
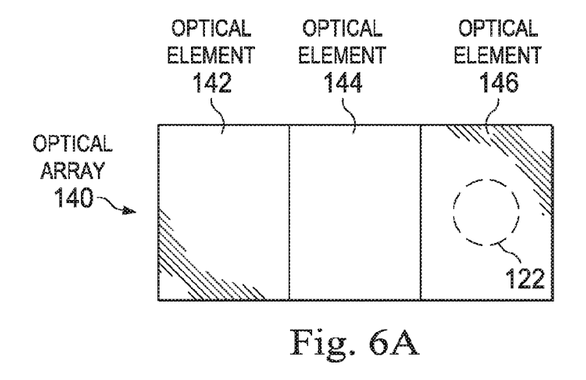
FIGS. 6A, 6B, and 6C are illustrations of an optical array of an ophthalmic illumination system.
Figure 6B:
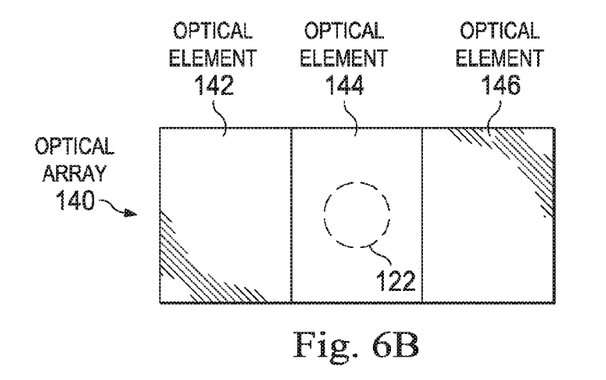
Figure 6C:
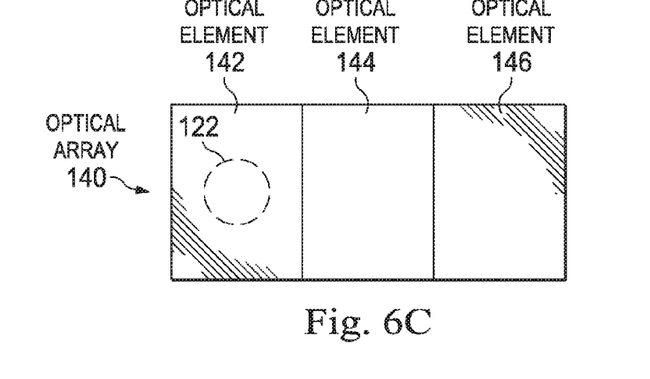

FIGS. 6A-6C can be front views of the optical array 170 illustrating relative alignment the light beam 122 and the optical elements 142, 144, 146. The optical elements 142, 144, 146 can be similarly sized and shaped. The optical elements 142, 144, 146 can be sized and shaped for a whole cross-section of the light beam 122 to respectively interact therewith. The optical array 140 can be moved as described herein while maintaining proper alignment of the light beam 122 with respect to the optical elements 142, 144, 146. For example, the light beam 122 can be centered within the optical elements 142, 144, 146 to facilitate transmission and reflection of the light beam 122. The light beam 122 can interact with the optical element 146 in FIG. 6A. Activation of the drive mechanism 170, actuation of the coupling mechanism 160, movement of the movable support 150, and corresponding movement of the optical array 140 can cause the light beam 122 to be selectively incident upon the optical element 144 (FIG. 6B) and the optical element 142 (FIG. 6C). The optical elements 142, 144, 146 can each reflect and transmit different amounts of the light beam 122. The optical array 140 can be moved in response to a user input based on the illumination needs of the user. For example, the user can determine the amount of light to the directed to each of the ports 112 and 114. The user can provide a user input at an input device 220 (FIG. 1) indicating the amount of light to the directed to each of the ports 112 and 114. In response to the user input, the computing device 210 can generate a control signal for the drive mechanism 170. The drive mechanism 170 can cause movement of the optical array 140 such that the light beam 122 is selectively incident upon the optical element 142, 144, or 146 that will direct the desired amount of light to each of the ports 112 and 114.

The optical array 140 can be variously arranged. For example, the optical array 140 of FIG. 7 can include optical elements 142, 144. The optical elements 142, 144 can be similarly sized and shaped. The optical elements 142, 144 can be relatively larger than the optical elements 142, 144, 146 of FIGS. 6A-6C. The light beam 122 can be incident on the optical element 144. Movement of the optical array 140 can cause the light beam 122 to be selectively incident on the optical element 140.

Figure 7:
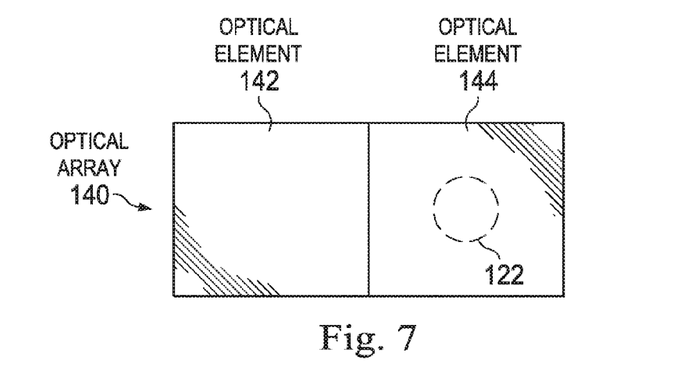
FIG. 7 is an illustration of an optical array of an ophthalmic illumination system.
Figure 8:
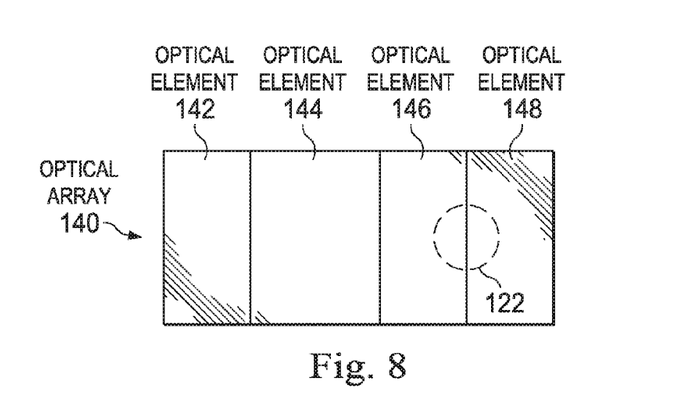
FIG. 8 is an illustration of an optical array of an ophthalmic illumination system.
Figure 9:
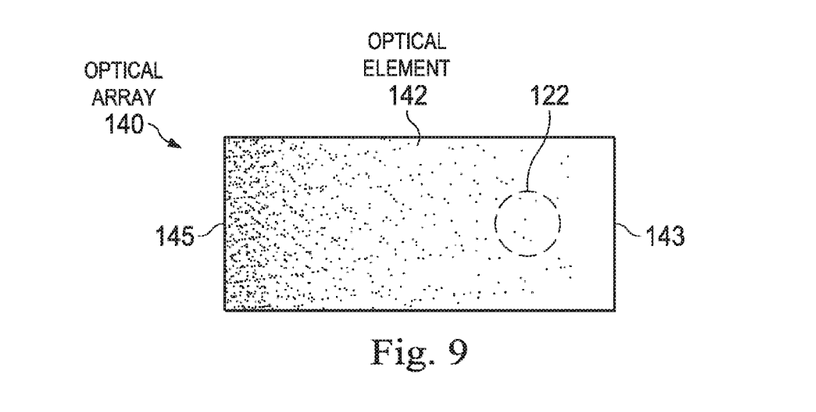
FIG. 9 is an illustration of an optical array of an ophthalmic illumination system.

The optical array 140 of FIG. 7 can include optical elements 142, 144, 146, 148. The optical elements 142, 144, 146, 148 can be unequally sized. For example, the optical element 142 can be relatively narrower than the optical elements 144, 146, 148. The optical element 144 can be relatively wider than the optical elements 142, 146, 148. The light beam 122 can be positioned to interact with both the optical elements 146 and 148. The properties of the optical elements 146 and 148 can be such that such simultaneous interaction with the light beam 122 can provide desirable properties for the reflected and the transmitted amounts of the light.

Generally, the optical elements 142, 144, 146, 148 can be sized, shaped, and arranged in any manner to facilitate interaction with the light beam 122. The optical array 140 of FIG. 9, for example, includes an optical element 142. The coating or embedded particles can be disposed on the optical element 142 as a gradient. Continuous variation in the amount of reflected and transmitted light can be obtained as optical array 140 moves relative to the light beam 122. For example, when the optical beam 122 interacts nearer to a side 143 of the optical element 142, the light beam 122 can be completely or nearly completely transmitted, with little to no reflection. When the optical beam 122 interacts nearer to a side 145 of the optical element 142, the light beam 122 can be completely or nearly completely reflected, with little to no reflection.

Referring to FIG. 1, the illumination subsystem 110, the light source 120, the beam guide 130, and/or the computing device 210 can be integrated in the surgical console 240. The surgeon can utilize the surgical console 240 to control one or more parameters associated with the ophthalmic surgical procedure. One or more components of the surgical console 240 can be coupled to and/or disposed within a housing. The housing can be mobile such that it can be positioned proximate to the patient during the ophthalmic surgical procedure. The housing can include pneumatic, optical, fluid, and/or electrical supply lines facilitating communication between components of the ophthalmic illumination system 100.

The computing device 200 can be in communication with the illumination subsystem 110, including the light source 120 and the drive mechanism 170. The computing device 200 can also be in communication with the input device 220. The computing device 200 can be configured generate and transmit control signals to and/or receive input or status signals from the components of the ophthalmic illumination system 100. For example, the computing device 200 can control activation and deactivation of the light source 120, activation and deactivation of the drive mechanism 170, selective transmission of light to the ports 112, 114, selective transmission of light by the optical fibers 262, 272, as well as the intensity, wavelength, and/or other characteristics of light output by the light source 120. In that regard, the light source 120 and the drive mechanism 170 can be in electrical communication with the computing device 210. The computing device 210 can include a processing circuit having a processor 212 and a memory 214. The processor 212 can execute computer instructions, such as those stored on the memory 214, to control various components of the ophthalmic illumination system 100. The processor 212 can be a targeted device controller and/or a microprocessor. The memory 214, such as semiconductor memory, RAM, FRAM, or flash memory, can interface with the processor 212. As such, the processor 212 can write to and read from the memory 214, and perform other common functions associated with managing memory 214. The processing circuit of the computing device 210 can be an integrated circuit with power, input, and output pins capable of performing logic functions. The computing device 210 can output display data to the display device 230 in communication with therewith. The display device 230 can be configured to display data relating to system operation and performance during an ophthalmic surgical procedure.

A probe subsystem 252 can be in electrical communication with the computing device 210. The probe subsystem 252 can include various components facilitating operation of the probe 250. The user can utilize the probe 250 within the surgical field to perform one or more surgical maneuvers. For example, the probe 250 can be a cutting probe, a vitrectomy probe, a phacoemulsification probe, a laser probe, an ablation probe, a vacuum probe, a flushing probe, scissors, forceps, an aspiration device, and/or other suitable surgical device. The probe 250 can be in mechanical, electrical, pneumatic, fluid, and/or other suitable communication with the probe subsystem 252.

The input device 220 can be in communication with the computing device 210. The input device 220 can be configured to allow the user to control ophthalmic illumination system 100, including activation of the drive mechanism 170, movement of the movable support 150, movement of the optical array 140, selection of one or more of the optical elements 142, 144, 146, 148, interaction of the light beam 122 with the selected optical element(s) 142, 144, 146, 148, the respective amounts of light associated with the transmitted beam 124 and the reflected beam 126, activating/deactivating the light source 120, and/or other features described herein. The input device 220 can comprise any of a variety of ON/OFF switches, buttons, toggles, wheels, digital controls, touchscreen controls, or other user interface components. The input device 220 can be integrally disposed on the surgical console 240. The display device 230 can be the input device 220. The input device 162 can be a distinct component, such as, by way of non-limiting example, a surgical footswitch, a remote control device, a touchscreen control device, and/or another computing device. The input device 220 can generate and transmit input signals based on the received user input. The computing device 210 can receive and process the input signal. The computing device 210 can generate and transmit control signals to the illumination subsystem 110, the light source 120, the drive mechanism 170, the probe subsystem 172, and the display device 168. For example, the user can provide a user input at the input device 180 to indicate the respective amounts of light to be available at each of the ports 112, 114. For example, the user input can specify 50% of the light beam 122 at the port 112 and 50% at the port 114. In response to the user input, the computing device 210 can generate and transmit a control signal to move the movable support 150 and the optical array 140 such that the optical element that provides the desired amounts of light at the ports 112, 114 interacts with the light beam 122. The optical array can guide the transmitted beam 124 and the reflected beam 126 having the desired properties to the ports 112, 114, respectively.

Embodiments as described herein can provide devices, systems, and methods of selectively guiding splitting and guiding light to ports of a housing of a surgical console and/or an illumination subsystem. Light from an incident beam can be split by an optical array having multiple optical components that reflect and transmit different amounts of light. The examples provided above can be exemplary in nature and not limiting. One skilled in the art may readily devise other systems consistent with the disclosed embodiments intended to be within the scope of this disclosure. As such, the application can be limited only by the following claims.

The invention claimed is:

1. An ophthalmic illumination apparatus, comprising:
a movable support;
an optical array coupled to the movable support and positioned to interact with a light beam from a light source, the optical array including first and second optical elements, wherein the first optical element is configured to reflect and transmit first associated amounts of the light beam, and wherein the second optical element is configured to reflect and transmit second associated amounts of the light beam different than the first optical element; and
a drive mechanism coupled to the movable support, wherein the drive mechanism is configured to cause the movable support to selectively move the optical array such that the light beam is selectively incident upon one of the first optical element or the second optical element.

2. The apparatus of claim 1, wherein:
the drive mechanism comprises a motor; and
the motor is coupled to the movable support via a coupling mechanism.

3. The apparatus of claim 2, wherein the coupling mechanism includes:
a belt and pulley system coupled to the motor and the movable support.

4. The apparatus of claim 2, wherein the coupling mechanism includes:
a rack coupled to the movable support; and
a pinion coupled to the motor and configured to engage the rack.

5. The apparatus of claim 2, wherein the coupling mechanism includes:
a lead screw coupled to the motor; and
a bearing block coupled to the movable support and configured to move along the lead screw.

6. The apparatus of claim 5, wherein:
the bearing block is coupled to the movable support via a dampening mechanism configured to minimize vibrations associated at least one of the drive mechanism or the coupling mechanism.

7. The apparatus of claim 1, further comprising:
a stabilizer positioned adjacent to the optical array and configured to stabilize the optical array while moving.

8. The apparatus of claim 1, further comprising:
a position sensor configured to determine a position of at least one of the optical array or the drive mechanism.

9. The apparatus of claim 1, further comprising:
a input device configured to receive user input to move the optical array; and
a computing device in communication with the input device and configured to output a control signal to the drive mechanism in response to the user input.

10. The apparatus of claim 1, further comprising:
a housing within which the movable support, the optical array, and the drive mechanism are positioned, wherein the housing further includes first and second ports, each of the first and second ports configured to interface with an optical fiber, and wherein the reflected portion of the light beam is directed to the first port and the transmitted portion of the light beam is directed to the second port.

11. A method of ophthalmic surgical illumination, the method comprising:
guiding, using an optical array, a reflected portion of a light beam from a light source and a transmitted portion of the light beam from the light source, the optical array including first and second optical elements, wherein the first optical element is configured to reflect and transmit first associated amounts of the light beam, and wherein the second optical element is configured to reflect and transmit second associated amounts of the light beam different than the first optical element; and
moving the optical array by moving a movable support using a drive mechanism, the optical array coupled to the movable support such that the light beam is selectively incident upon one of the first optical element or the second optical element.

12. The method of claim 11, wherein moving the optical array includes:
actuating a coupling mechanism coupling the movable support and the drive mechanism.

13. The method of claim 11, wherein actuating a coupling mechanism includes actuating at least one of a:
a belt and pulley system;
a rack and pinion system; and
a lead screw and bearing block system.

14. The method of claim 11, moving the optical array includes:
moving the optical array in response to a user input received at an input device.

* * * * *